(12) United States Patent
Kroll et al.

(10) Patent No.: US 11,224,474 B2
(45) Date of Patent: Jan. 18, 2022

(54) SYSTEM FOR MANAGING HIGH IMPEDANCE CHANGES IN A NON-THERMAL ABLATION SYSTEM FOR BPH

(71) Applicant: Prostacare Pty Ltd, Sydney (AU)

(72) Inventors: Mark W. Kroll, Crystal Bay, MN (US); Kai Kroll, Minneapolis, MN (US)

(73) Assignee: Prostacare Pty Ltd

( * ) Notice: Subject to any disclaimer, the term of this patent is extended or adjusted under 35 U.S.C. 154(b) by 295 days.

(21) Appl. No.: 16/287,551

(22) Filed: Feb. 27, 2019

(65) Prior Publication Data

US 2020/0022748 A1 Jan. 23, 2020

Related U.S. Application Data

(60) Provisional application No. 62/636,636, filed on Feb. 28, 2018.

(51) Int. Cl.
*A61B 18/12* (2006.01)
*A61B 18/14* (2006.01)
*A61B 18/00* (2006.01)

(52) U.S. Cl.
CPC .......... *A61B 18/1233* (2013.01); *A61B 18/14* (2013.01); *A61B 2018/00547* (2013.01);
(Continued)

(58) Field of Classification Search
CPC . A61B 18/1206; A61B 18/1233; A61B 18/14; A61B 18/1485; A61B 2018/00107;
(Continued)

(56) References Cited

U.S. PATENT DOCUMENTS 3,698,394 A 10/1972 Piper et al.
3,933,616 A 1/1976 Beer
(Continued)

FOREIGN PATENT DOCUMENTS

EP 1080731 A2 3/2001
EP 2326274 B1 8/2009
(Continued)

OTHER PUBLICATIONS

A. Plesnicar, G. Sersa, L. Vodovnik, J. Jancar, L. Zaletel-Kragelj and S. Plesnicar. Electric Treatment of Human Melanoma Skin Lesions with Low Level Direct Electric Current: An Assessment of Clinical Experience Following a Preliminary Study in Five Patients, European Journal of Surgery 1994; Suppl 574:45-49.
(Continued)

*Primary Examiner* — Michael F Peffley
(74) *Attorney, Agent, or Firm* — Patterson Thuente Pedersen, P.A.

(57) ABSTRACT

A protection circuit for a direct-current (DC) ablation prostate therapy system. The protection circuit is selectively coupled to a power source that provides DC constant current to a plurality of electrodes in a catheter configured to deliver DC ablation therapy to prostate tissue. The protection circuit is controlled by a controller and a switching circuit to buffer energy from the power source in response to a monitoring circuit that monitors at least one parameter of the DC ablation therapy, such as voltage or impedance. The controller is configured to selectively activate the switching circuit based on the monitoring circuit detecting an undesirable increase in the energy delivered for the DC ablation therapy.

7 Claims, 5 Drawing Sheets

(52) U.S. Cl.
CPC ............... *A61B 2018/00577* (2013.01); *A61B 2018/1266* (2013.01)

(58) Field of Classification Search
CPC ........... A61B 2018/00547; A61B 2018/00577; A61B 2018/00755; A61B 2018/00875; A61B 2018/00892; A61B 2018/124; A61B 2018/1266; A61B 2018/143; A61B 2018/1432
See application file for complete search history.

(56) References Cited

U.S. PATENT DOCUMENTS

| | | | |
|---|---|---|---|
| 4,003,379 A | 1/1977 | Ellinwood, Jr. | |
| 4,026,304 A | 5/1977 | Levy | |
| 4,289,135 A | 9/1981 | Nordenstrom et al. | |
| 4,572,214 A | 2/1986 | Nordenstrom et al. | |
| 4,639,244 A | 1/1987 | Rizk et al. | |
| 4,679,561 A | 7/1987 | Doss | |
| 4,682,596 A | 7/1987 | Bales et al. | |
| 4,721,123 A | 1/1988 | Cosentino et al. | |
| 4,919,138 A | 4/1990 | Nordenstrom | |
| 4,974,595 A | 12/1990 | Nordenstrom | |
| 5,002,558 A | 3/1991 | Klein et al. | |
| 5,026,371 A | 6/1991 | Rydell et al. | |
| 5,058,605 A | 10/1991 | Slovak | |
| 5,084,154 A | 1/1992 | Wakizoe et al. | |
| 5,098,843 A | 3/1992 | Calvin | |
| 5,281,218 A | 1/1994 | Imran | |
| 5,304,214 A | 4/1994 | DeFord et al. | |
| 5,314,451 A | 5/1994 | Mulier | |
| 5,314,457 A | 5/1994 | Jeutter et al. | |
| 5,370,675 A | 12/1994 | Edwards et al. | |
| 5,431,625 A | 7/1995 | Fabian et al. | |
| 5,458,627 A | 10/1995 | Baranowski | |
| 5,482,054 A | 1/1996 | Slater et al. | |
| 5,501,662 A | 3/1996 | Hofmann | |
| 5,507,724 A | 4/1996 | Hofmann et al. | |
| 5,529,574 A | 6/1996 | Frackelton | |
| 5,536,240 A | 7/1996 | Edwards et al. | |
| 5,536,267 A | 7/1996 | Edwards et al. | |
| 5,558,673 A | 9/1996 | Edwards et al. | |
| 5,584,872 A | 12/1996 | LaFontaine et al. | |
| 5,611,350 A | 3/1997 | John | |
| 5,630,426 A | 5/1997 | Eggers et al. | |
| 5,672,153 A | 9/1997 | Lax et al. | |
| 5,674,267 A | 10/1997 | Mir et al. | |
| 5,680,860 A | 10/1997 | Imran | |
| 5,701,895 A | 12/1997 | Prutchi et al. | |
| 5,718,686 A | 2/1998 | Davis | |
| 5,807,306 A | 9/1998 | Shapland et al. | |
| 5,810,764 A | 9/1998 | Eggers et al. | |
| 5,820,548 A | 10/1998 | Sieben et al. | |
| 5,868,741 A | 2/1999 | Chia et al. | |
| 5,869,326 A | 2/1999 | Hofmann | |
| 5,919,187 A | 7/1999 | Guglielmi et al. | |
| 5,931,858 A | 8/1999 | Mackey | |
| 5,983,131 A | 11/1999 | Weaver et al. | |
| 5,985,305 A | 11/1999 | Peery et al. | |
| 5,993,434 A | 11/1999 | Dev et al. | |
| 6,009,345 A | 12/1999 | Hofmann | |
| 6,016,452 A | 1/2000 | Kasevich | |
| 6,021,347 A | 2/2000 | Herbst et al. | |
| 6,023,638 A | 2/2000 | Swanson | |
| 6,049,733 A | 4/2000 | Phipps et al. | |
| 6,051,017 A | 4/2000 | Loeb et al. | |
| 6,162,219 A | 12/2000 | Nilsson et al. | |
| 6,165,206 A | 12/2000 | Tu | |
| 6,169,924 B1 | 1/2001 | Meloy et al. | |
| 6,171,787 B1 | 1/2001 | Wiley | |
| 6,174,309 B1 | 1/2001 | Wrublewski et al. | |
| 6,179,833 B1 | 1/2001 | Taylor | |
| 6,238,393 B1 | 5/2001 | Mulier et al. | |
| 6,245,068 B1 | 6/2001 | Olson et al. | |
| 6,269,270 B1 | 7/2001 | Boveja | |
| 6,273,886 B1 | 8/2001 | Edwards | |
| 6,278,895 B1 | 8/2001 | Bernard | |
| 6,366,808 B1 | 4/2002 | Schroeppel et al. | |
| 6,379,353 B1 | 4/2002 | Nichols | |
| 6,387,075 B1 | 5/2002 | Stiviand et al. | |
| 6,391,026 B1 | 5/2002 | Hung et al. | |
| 6,402,745 B1 | 6/2002 | Wilk | |
| 6,419,673 B1 | 7/2002 | Edwards et al. | |
| 6,464,699 B1 | 10/2002 | Swanson | |
| 6,591,133 B1 | 7/2003 | Joshi | |
| 6,595,989 B1 | 7/2003 | Schaer | |
| 6,599,274 B1 | 7/2003 | Kucharczyk et al. | |
| 6,600,953 B2 | 7/2003 | Flesler et al. | |
| 6,607,528 B1 | 8/2003 | Quick et al. | |
| 6,626,899 B2 | 9/2003 | Houser et al. | |
| 6,638,273 B1 | 10/2003 | Farley et al. | |
| 6,638,275 B1 | 10/2003 | McGaffigan et al. | |
| 6,708,066 B2 | 3/2004 | Herbst et al. | |
| 6,713,291 B2 | 3/2004 | King et al. | |
| 6,733,485 B1 | 5/2004 | Whitehurst et al. | |
| 6,738,663 B2 | 5/2004 | Schroeppel et al. | |
| 6,901,296 B1 | 5/2005 | Whitehurst et al. | |
| 6,952,615 B2 | 10/2005 | Satake | |
| 7,079,890 B2 | 7/2006 | Ahn et al. | |
| 7,412,285 B2 | 8/2008 | Schroeppel et al. | |
| 7,556,624 B2 | 7/2009 | Laufer et al. | |
| 7,720,549 B2 | 5/2010 | Schroeppel et al. | |
| 7,742,811 B2 | 6/2010 | Schroeppel et al. | |
| 7,837,670 B2 | 11/2010 | Barath | |
| 8,014,854 B2 | 9/2011 | Schroeppel et al. | |
| 8,024,048 B2 | 9/2011 | Schroeppel et al. | |
| 9,211,155 B2 | 12/2015 | Fruland et al. | |
| 9,597,145 B2 | 3/2017 | Nelson et al. | |
| 10,004,551 B2 | 6/2018 | Burnett | |
| 10,085,800 B2 | 10/2018 | Nelson et al. | |
| 10,575,899 B2 | 3/2020 | Fruland et al. | |
| 10,736,689 B2 | 8/2020 | Sundquist et al. | |
| 10,842,555 B2 | 11/2020 | Holtz et al. | |
| 10,939,957 B2 | 3/2021 | Nelson et al. | |
| 2001/0001314 A1 | 5/2001 | Davison et al. | |
| 2001/0021868 A1 | 9/2001 | Herbst et al. | |
| 2001/0034518 A1 | 10/2001 | Edwards et al. | |
| 2002/0002329 A1 | 1/2002 | Avitall | |
| 2002/0026188 A1 | 2/2002 | Balbierz et al. | |
| 2002/0077676 A1* | 6/2002 | Schroeppel | A61N 1/403 607/75 |
| 2002/0111618 A1 | 8/2002 | Stewart et al. | |
| 2002/0115957 A1 | 8/2002 | Sun et al. | |
| 2002/0183735 A1 | 12/2002 | Edwards et al. | |
| 2003/0130711 A1 | 7/2003 | Pearson et al. | |
| 2003/0191504 A1 | 10/2003 | Meadows et al. | |
| 2003/0002123 A1 | 11/2003 | Pearson et al. | |
| 2004/0010290 A1 | 1/2004 | Schroeppel et al. | |
| 2004/0030334 A1 | 2/2004 | Quick et al. | |
| 2004/0059326 A1 | 3/2004 | Flores | |
| 2004/0172089 A1 | 9/2004 | Whitehurst et al. | |
| 2004/0254618 A1 | 12/2004 | Schroeppel et al. | |
| 2005/0000443 A1 | 1/2005 | Ward et al. | |
| 2005/0004507 A1 | 1/2005 | Schroeppel et al. | |
| 2005/0010203 A1 | 1/2005 | Edwards et al. | |
| 2005/0054994 A1 | 3/2005 | Cioanta et al. | |
| 2005/0080409 A1 | 4/2005 | Young et al. | |
| 2005/0131508 A1 | 6/2005 | Garabedian et al. | |
| 2005/0159742 A1 | 7/2005 | Lesh | |
| 2005/0182449 A1 | 8/2005 | Auge et al. | |
| 2005/0197657 A1 | 9/2005 | Goth et al. | |
| 2005/0222623 A1 | 10/2005 | Kroll et al. | |
| 2005/0222646 A1 | 10/2005 | Kroll et al. | |
| 2005/0228373 A1 | 10/2005 | Kelly et al. | |
| 2005/0245923 A1 | 11/2005 | Christopherson et al. | |
| 2005/0283125 A1 | 12/2005 | Barkhahn et al. | |
| 2005/0288730 A1 | 12/2005 | Deem et al. | |
| 2006/0025756 A1 | 2/2006 | Francischelli et al. | |
| 2006/0095032 A1 | 5/2006 | Jackson et al. | |
| 2006/0235286 A1 | 10/2006 | Stone et al. | |
| 2006/0259027 A1 | 11/2006 | Kwan et al. | |
| 2007/0016067 A1 | 1/2007 | Webster, III et al. | |
| 2007/0073391 A1 | 3/2007 | Bourang et al. | |
| 2007/0179491 A1 | 8/2007 | Kratoksa et al. | |

(56) References Cited

U.S. PATENT DOCUMENTS

| | | |
|---|---|---|
| 2007/0191925 A1 | 8/2007 | Dorn |
| 2007/0255207 A1 | 11/2007 | Hangai et al. |
| 2007/0260234 A1 | 11/2007 | McCullagh et al. |
| 2008/0021275 A1 | 1/2008 | Tearney et al. |
| 2008/0021445 A1 | 1/2008 | Elmouelhi et al. |
| 2008/0027379 A1 | 1/2008 | Wilkins |
| 2008/0071262 A1 | 3/2008 | Azure |
| 2008/0132885 A1 | 6/2008 | Rubinsky et al. |
| 2008/0161804 A1 | 7/2008 | Rioux et al. |
| 2008/0243116 A1 | 10/2008 | Anderson |
| 2009/0024075 A1 | 1/2009 | Schroeppel et al. |
| 2010/0049031 A1 | 2/2010 | Fruland et al. |
| 2010/0049188 A1 | 2/2010 | Nelson et al. |
| 2010/0049192 A1 | 2/2010 | Holtz et al. |
| 2010/0168777 A1 | 7/2010 | Stangenes et al. |
| 2011/0106072 A1 | 5/2011 | Sundquist et al. |
| 2011/0166569 A1 | 7/2011 | Whayne et al. |
| 2011/0208022 A1 | 8/2011 | Brawer et al. |
| 2011/0224663 A1* | 9/2011 | Heim ............... A61B 18/1206 606/33 |
| 2012/0203307 A1 | 8/2012 | Schroeppel et al. |
| 2014/0005676 A1 | 1/2014 | Shelton, IV et al. |
| 2016/0018403 A1 | 6/2016 | Shelton, IV et al. |
| 2016/0206370 A1 | 7/2016 | Fruland et al. |
| 2017/0231693 A1 | 8/2017 | Nelson et al. |
| 2019/0021779 A1* | 1/2019 | Govari ............... A61B 18/1492 |
| 2019/0105103 A1 | 4/2019 | Fruland et al. |
| 2019/0159834 A1 | 5/2019 | Gilmour et al. |

FOREIGN PATENT DOCUMENTS

| | | |
|---|---|---|
| EP | 2326273 | 6/2011 |
| EP | 2326274 | 6/2011 |
| WO | WO 1997/036632 A1 | 10/1997 |
| WO | WO 1998/047562 A1 | 10/1998 |
| WO | WO 2001/052931 A1 | 7/2001 |
| WO | WO 2001/062336 A1 | 8/2001 |
| WO | WO 2002/098501 A2 | 12/2002 |
| WO | WO 2005/086683 A2 | 9/2005 |
| WO | WO 2006/042117 A2 | 4/2006 |
| WO | WO 2008/083407 A1 | 7/2008 |
| WO | WO 2010/022275 A1 | 2/2010 |
| WO | WO 2010/022278 A1 | 2/2010 |
| WO | WO 2010/081730 A1 | 7/2010 |

OTHER PUBLICATIONS

A.L. Vandenbogaerde, E.M. Delaey, A.M. Vantieghem, B.E. Himpens, W.J. Merlevede, P. A. de Witte, Abstract of Cytotoxicity and Antiproliferative Effect of Hypericin and Derivatives After Photosensitization. Photochem Photobiol Jan. 1998;67(1):119-25.

B. Wolf, M. Brischwein, W. Baumann, R. Ehret, T. Henning, M. Lehmann, A. Schwinde. Microsensor-Aided Measurements of Cellular Signalling and Metabolism on Tumor Cells, Tumor Biology 1998; 19:374-383.

B.N. Singh and C. Dwivedi. Antitumor Drug Delivery by Tissue Electroporation, Anti-Cancer Drugs 1999, 10, pp. 139-146.

Belehradek, J.J., Orlowski, S., Raimiriz, L.H., Pron, G., Poddevin, B. and Mir, L.M., "Electropermeabilization of cells and tissues assessed by the qualitative and quantitative electroloading of bleomycin", Biochem. Biophys. Acta, vol. 1190, pp. 155-163, 1994.

Berendson J. Simonsson D. Electrochemical aspects of treatment of tissue with direct current. Eur J Surg 1994: Suppl 574: 111-115.

Buchwald H, Rohde TD. Implantable pumps. Recent progress and anticipated future advances. ASAIO J 1992; 38 No. 4: 772-778.

C. Hauton, M. Charbonnier, L. Cara and J.P. Salles, A New Type of Liposome for Electrochemical Treatment of Cancer: The Lipogelosomes, European Journal of Surgery 1994; Suppl 574: 117-119.

C.E. Humphrey, E.H. Seal. Biophysical Approach toward Tumor Regression in Mice, Science, vol. 130, 1959.

Chen B, Xie Z, Zhu F. Experimental study on electrochemical treatment of cancer in mice. Eur J Surg 1994: Suppl 574: 75-77.

Chou C, McDougall JA, Ahn C, Vora N. Electrochemical treatment of mouse and rat fibrosarcomas with direct current. Bioelectromagnetics 1997; 18: 14-24.

D. Liu, Y.L. Xin, B. Ge, F. Zhao, H.C. Zhso. Experimental Studies on Electrolytic Dosage of ECT for Dog's Oesophageal Injury and Clinical Effects of ECT for Oesopohageal Anastomotic Opening Stenosis and Oesophageal Carcinoma, European Journal of Surgery 1994; Suppl 574: 71-72.

D. Miklavcic, D. An, J. Belehradek, Jr., L.M. Mir. Abstract of Host's Immune Response in Electrotherapy of Murine Tumors by Direct Current, European Cytokine Network Sep. 1997;8(3):275-9.

D.M. Morris, M.D., A.A. Marino, Ph. D., and E. Gonzalez, M.D. Electrochemical Modification of Tumor Growth in Mice, Journal of Surgical Research 53, 306-309 (1992).

Damascelli B, Patelli G, Frigerio LF, Lanocita R, Di Tolla GD, Marchiano A., Spreafico C, Garbagnati F, Bonalumi MG, Monfardini L Ticha V, Prino A. First clinical experience with a high-capacity implantable infusion pump for continuous intravenous chemotherapy. Cardiovasc Intervent Radiol 1999; 22: 37-43.

E. Nilsson. Modelling of the Electrochemical Treatment of Tumours. Dissertation, Department of Chemical Engineering and Technology, Applied Electrochemistry, Royal Institute of Technology, Stockholm 2000.

Electro-Cancer Treatment, http://www.st-georg.com/ect.html, retrieved Oct. 25, 1999.

G. Sersa, M. Cemazar, D. Miklavcic and D. J. Chaplin, Tumor Blood Flow Modifying Effect of Electrochemotherapy with Bleomycin, Anticancer Research 19: 4017-4022 (1999).

G.D. O'Clock, Ph. D. (E.E.), P.E. The Effects of In Vitro Electrical Stimulation on Eukaryotic Cells: Suppression of Malignant Cell Proliferation, Journal of Orthomolecular Medicine, vol. 12, No. 3, 1997.

H. Gong, G. Liu. Effect of Electrochemical Therapy on Immune Functions of Normal and Tumour-Bearing Mice, European Journal of Surgery, Suppl 1994; (574): 73-74.

H. von Euler, Electrochemical Treatment of Tumours, Doctoral Thesis, Swedish University of Agricultural Sciences, Uppsala 2002.

Habal and Schauble. An implantable DC power unit for control of experimental tumor growth in hamsters. Medical Instrumentation 7 No. 5: 305-306. (1973).

Heruth KT, Medtronic SynchroMed drug administration system. Ann NY Acad Sci 1988; 531: 72-75.

Hofmann, Dev, Nanda, and Rabussay. electroporation therapy of solid tumors. Critical Reviews in therapeutic Drug Carrier Systems 16(6):523-569 (1999).

Hofmann, G.A., Dev. S.B., Dimmer, S. and Nanda, G.S., "Electroporation Therapy: A new approach to the treatment of head and neck cancer, IEEE Transactions on Biomedical Engineering", vol. 46, No. 6, pp. 752-759, 1999.

http://www.genetronics.com, retrieved Jul. 29, 2003.

J.C. Weaver. Electroporation: A General Phenomenom for Manipulating Cells and Tissues. J Cell Biochem 1993; 51 No. 4: 426-435.

K. Brandisky, I. Daskalov. Abstract of Electrical Field and Current Distributions in Electrochemotherapy, Bioelectrochemistry and Bioenergetics Feb. 1999; 48(1):201-8.

Kirsch DL, Lerner FN. Electromedicine: the other side of physiology. In: Innovations in pain management: a practical guide for clinicians. Winter Park, FL: GR Press, 1995.

L. Vodovnik, D. Miklavcic, G. Sersa. Modified Cell Proliferation Due to Electrical Currents, Medical and Biological Engineering and Computing, 1992, 30, CE21-CE28.

L.F. Glass, N.A. Fenske, M. Jaroszeski, R. Perrott, D.T. Harvey, D.S. Reintgen, R. Heller. Abstract of Bleomycin-Mediated Electrochemotherapy of Basal Cell Carcinoma, Journal of the American Academy of Dermatology Jan. 1996; 34(1):82-6.

L.H. Ramirez, S. Orlowski, D. An, G. Bindoula, R. Dzodic, P. Ardouin, C. Bognel, J. Belehradek Jr., J-N Munck, and L.M. Mir. Electrochemotherapy on Liver Tumours in Rabbits, British Journal of Cancer (1998) 77(12). 2104-2111.

Lao, Y., Ge, T., Zheng, X., Zhang, J. Hua, Y., Mao, S., Feng, X. Electrochemical therapy for intermediate and advanced liver cancer: a report of 50 cases. Eur J Surg 1994; Suppl 574: 51-53.

(56) References Cited

OTHER PUBLICATIONS

Li K, Xin Y, Gu Y, Xu B, Fan D. Ni B. Effects of direct current on dog liver: possible mechanisms for tumor electrochemical treatment. Bioelectromagnetics 1997; 18: 2-7.

M. Belehradek, C. Domenge, B. Luboinski, S. Orlowski, J. Belehradek, Jr., L.M. Mir. Abstract of Electrochemotherapy, A new antitumor treatment. First clinical phase I-II trial. Cancer Dec. 15, 1993; 72(12):3694-700.

M. Cemazar, G. Sersa and D. Miklavcic. Electrochemotherapy with Cisplatin in the Treatment of Tumor Cells Resistant to Cisplatin, Anticancer Research 18: 4463-4466 (1998).

M. Kraus and B. Wolf. Implications of Acidic Tumor Microenvironment for Neoplastic Growth and Cancer Treatment: A Computer Analysis, Tumor Biology 1996; 17: 133-154.

M. Kraus and B. Wolf. Physicochemical Microenvironment as Key Regulator for Tumor Microevolution, Invasion, and Immune Response: Targets for Endocytotechnological Approaches in Cancer Treatment, Endocytobiosis & Cell Research, 12, 133-156 (1998).

M. Wojcicki, R. Kostyrka, B. Kaczmarek, J. Kordowski, M. Romanowski, M. Kaminski, J. Klonek, S. Zielinski. Abstract of Electrochemical Therapy in Palliative Treatment of Malignant Dysphagia: A Pilot Study, Hepatogastroenterology Jan.-Feb. 1999;46(25):278-84.

M.A. Hamza, P.F. White, H.E. Ahmed, E.A. Ghoname. Abstract of Effect of the Frequency of Transcutaneous Electrical Nerve Stimulation on the Postoperative Opioid Analgesic Requirement and Recovery Profile, Anesthesiology Nov. 1999;91(5):1232-8.

M.B. Habal. Abstract of Effect of Applied DC Currents on Experimental Tumor Growth in Rats, Journal of Biomedical Materials Research, vol. 14, 789-801 (1980).

M.K. Schauble, M.B. Habal. Electropotentials of Tumor Tissues. Journal of Surgical Research 9: 9, 1969.

Matsushima Y, Takahashi E, Hagiwara K, Konaka C, Miura H, Kato H, Koshiishi Y. Clinical and experimental studies of anti-tumoural effects of electrochemical therapy (ECT) alone or in combination with chemotherapy. Eur J Surg 1994; Suppl 574: 59-67.

Mir LM, Orlowski S, Belehradek Jr J, Paoletti C. Electrochemotherapy potentiation of antitumour effect of bleomycin by local electric pulses. Eur J Cancer 1991; 27:68-72.

N. Raghunand. Abstract of pH and Chemotherapy, Symposium 240: The Tumour Microenvironment: Causes and Consequences of Hypoxia and Acidity, p. 5-6, held at the Novartis Foundation, London, 240 Oct. 10-12, 2000.

Nordenstrom B. Biologically closed electric circuits: activation of vascular interstitial closed electric circuits for treatment of inoperable cancer. Journal of Bioelectricity 1984; 3(162): 137-153.

Nordenstrom B. Preliminary clinical trials of electrophoretic ionization in the treatment of malignant tumors. IRCS Med Sc 1978; 6: 537.

Nordenstrom BEW, Eksborg, S., Beving, H. Electrochemical treatment of cancer. II: effect of electrophoretic influence on adriamycin. Am J Clin Oncol (CCT)1990; 13(1): 75-88.

Nordenstrom BEW. Biologically closed electric circuits: clinical, experimental and theoretical evidence for an additional circulatory system. Stockholm: Nordic Medical Publications, 1983.

Nordenstrom BEW. Electrochemical treatment of cancer. I: variable response to anodic and cathodic fields. Am J Clin Oncol (CCT) 1989; 12(6): 530-536.

Nordenstrom BEW. Survey of mechanisms in electrochemical treatment (ECT) of cancer. Eur J Surg 1994: Suppl 574: 93-109.

Okino, M. and Mohri, H. Effects of a high voltage electrical impulse and an anti-cancer drug on In Vivo growing tumors. Japanese Journal of Cancer Research, vol. 78, pp. 1319-1321, 1987.

Orlowski, S., Belehradek, J.J., Paoletti,C. and Mir, L.M. "Transient electropermeabilization of cells in culture increase of the cytotoxicity of anti-cancer drugs", Biochem, vol. 37, No. 24, pp. 4727-4733, 1988.

P. Vaupel, D.K. Kelleher, M. Hockel. Abstract of Oxygen Status of Malignant tumors: Pathogenesis of Hypoxia and Significance for Tumor Therapy. Semin Oncol Apr. 2001; 28(2 Suppl 8):29-35.

Quan, K. Analysis of the clinical effectiveness of 144 cases of soft tissue and superficial malignant tumors treated with electrochemical therapy. Eur J Surg 1994; Suppl 574: 37-40.

R.A. Gatenby. Abstract of Mathematical Models of Tumour Invasion Mediated by Transformation-Induced Alteration of Microenvironment pH, Symposium 240: The Tumour Microenvironment: Causes and Consequences of Hypoxia and Acidity, p. 2-3, held at the Novartis Foundation, London, 240 Oct. 10-12, 2000.

Ranade VV. Drug delivery systems. 4. Implants in drug delivery. J Clin Pharmacol 1990; 30 No. 10: 871-889.

Reis A, Henninger T. Zerstorung maligner Wachstumsenergie durch anodische Oxydation, Kim Wochenschrift 1951; _: 39.

S. Seguchi, S. Kawauchi, Y. Morimoto, T. Arai, H. Asanuma, M. Hayakawa, M. Kikuchi. Abstract of Critical Parameters in the Cytotoxicity of Photodynamic Therapy Using a Pulsed Laser. Lasers Med Sci 2002, 17(4):265-71.

S.A. Grossman, P.S. Staats, Abstract of Current Management of Pain in Patients with Cancer. Oncology (Huntingt) Mar. 1994; 8(3):93-107.

S.L. David, D.R. Absolom, C.R. Smith, J. Gams, and M.A. Herbert. Effect of Low Level Direct Current on In Vivo Tumor Growth in Hamsters, Cancer Research 45, 5625-5631, Nov. 1985.

Samuelsson, Harnek, Ewers, Jonsson. Electrochemical and megavolt treatment of rat tumors. Eur J Surg Suppl 574:69-70. (1994).

Schauble MK, Mutaz HB, Gallick HD. Inhibition of experimental tumor growth in hamsters by small direct currents. Arch Pathol Lab Med 1977; 101: 294.

Schecter, DC. "Containment of Tumors Through Electricity." PACE 1979. vol. 2, pp. 100-114.

Semrov and Miklacic. Calculation of the electrical parameters in electrochemistry of solid tumors in mice. Comp Biol Med 28:439-448. (2000).

Sersa, et al. Improvement of Combined modality therapy with cisplatin and radiation using electroporation of tumors. Int J. Radiation Oncology Biol. Phys. vol. 46, No. 4:1037-1041. (2000).

Song Y, Li C, Li Y, Song Q. Chang B, Song L. Liu C. Wang T. Electrochemical therapy in the treatment of malignant tumors on the body surface. Eur J Surg 1994; Suppl 574: 41-43.

Song, L., Liu, C., Zhang, B., Wang, T., Song, Y., Li, Y. Electrochemical therapy (ECT) for thyroid adenoma during acupuncture anaesthesia: analysis of 46 patients. Eur J Surg 1994; Suppl 574: 79-81.

Srinivasan S, Gahen Jr. GL, Stoner GE. Electrochemistry in the biomedical sciences. In: Bloom H, Gutmann F (eds): Electrochemistry the last thirty and the next thirty years. New York: Plenum Press, 1977.

T. Nishi, S.B. Dev., K. Yoshizato, J. Kuratsu, Y. Ushio. Abstract of Treatment of Cancer Using Pulsed Electric Field in Combination With Chemotherapeutic Agents or Genes, Human Cell Mar. 1997;10(1):81-6.

T.V. Taylor, P. Engler, B.R. Pullan and S. Holt. Ablation of Neoplasia by Direct Current, British Journal of Cancer (1994), 70, 342-345.

Turler, Schaefer, et al. Local treatment of hepatic metastases with low level direct electric current: experimental results. Scand J Gastroenterol. 3:322-328. (2000).

Vogelzang NJ, Ruane M, DeMeester TR. Phase I trial of an implanted battery-powered, programmable drug delivery system for continuous doxorubicin administration. J Clin Oncol 1985; 3 No. 3: 407-414.

W.R. Panje, M.P. Hier, G.R. Garman, E. Harrell, A. Goldman, I. Bloch. Abstract of Electroporation Therapy of Head and Neck Cancer, Annals of Otology, Rhinology and Laryngology Sep. 1998; 107(9 Pt 1): 779-85.

Wang, H. Electrochemical therapy of 74 cases of liver cancer. Eur J Surg 1994; Suppl 574: 55-57.

Wigness BD, Dorman FD, Robinson Jr HJ, Arendt EA, Oegema Jr TR,Rohde TD, Buchwald H. Catheter with an anchoring tip for chronic joint capsule perfusion. ASAIO Trans. 1991; 37 No. 3: M290-292.

Wolf B, Kraus M, and Sieben U, "Potential of microsensor-based feedback bioactuators for biophysical cancer treatment," Biosensors and Bioelectronics, vol. 12, No. 4, pp. 301-309, 1997.

(56) References Cited

OTHER PUBLICATIONS

X.Z. Lin, C.M. Jen, C.K. Choud, D.S. Chou, M.J. Sung, T.C. Chou. Saturated Saline Enhances the Effect of Electrochemical Therapy. Digestive Diseases and Sciences 2000: 45(3): 509-514.

Xin Y, Xue F, Ge B, Zhao F, Shi B, Zhang W. Electrochemical treatment of lung cancer. Bioelectromagnetics 1997; 18: 8-13.

Xin, Y. Organisation and spread of electrochemical therapy (ECT) in China. Eur J Surg 1994; Suppl 577: 25-30.

Y. Yen, J.R. Li, B.S. Zhou, F. Rojas, J. Yu and C.K. Chou. Electrochemical Treatment of Human KB Cells In Vitro, Bioelectromagnetics 20:34-41 (1999).

Y.L. Xin, D. Liu. Electrostatic Therapy (EST) of Lung Cancer and Pulmonary Metastasis: Report of 15 Cases. European Journal of Surgery 1994; Suppl 574: 91-92.

Y.L. Xin, F.Z. Xue, F.G. Zhao. Effectiveness of Electrochemical Therapy in the Treatment of Lung Cancers of Middle and Late Stage, Chinese Medical Journal 1997 110(5): 379-383.

Yokoyama, M., Itaoka, T., Nakajima, H., Ikeda, T., Ishikura, T., Nitta, S. [The use of direct current in the local destruction of cancer tissues]. Gan To Kagaku Ryoho Apr. 1989; 16(4 Pt 2-2): 1412-1417.

Gravante et al., "Experimental Application of Electrolysis in the Treatment of Liver and Pancreatic Tumours: Principles, Preclinical and Clinical Observations and Future Perspectives," Elsevier Ltd., ScienceDirect, dated Dec. 7, 2009, 15 pages.

Dalziel et al., "Let-Go Currents and Voltages," Transactions of the American Institute of Electrical Engineers, Part II: Applications and Industry, 75(2): pp. 49-56, 1956.

PCT/US2019/019788, PCT International Search Report and Written Opinion dated May 14, 2019, 6 pages.

Application and File history for U.S. Appl. No. 12/544,112, filed Aug. 19, 2009. Inventors: Fruland et al.

Application and File history for U.S. Appl. No. 14/969,889, filed Dec. 15, 2015. Inventors: Fruland et al.

Application and File history for U.S. Appl. No. 12/544,119, filed Aug. 19, 2009. Inventors: Sundquist et al.

Application and File history for U.S. Appl. No. 12/544,127, filed Aug. 19, 2009. Inventors: Holtz et al.

Application and File history for U.S. Appl. No. 12/544,134, filed Aug. 19, 2009. Inventors: Nelson et al.

Application and File history for U.S. Appl. No. 15/455,358, filed Mar. 10, 2016. Inventors: Nelson et al.

Application and File history for U.S. Appl. No. 16/148,756, filed Oct. 1, 2018. Inventors: Nelson et al.

Application and File history for U.S. Appl. No. 16/201,642, filed Nov. 27, 2018. Inventors: Gilmour et al.

\* cited by examiner

SYSTEM FOR MANAGING HIGH IMPEDANCE CHANGES IN A NON-THERMAL ABLATION SYSTEM FOR BPH

RELATED APPLICATION

This application claims the benefit of U.S. Provisional Application No. 62/636,636 filed Feb. 28, 2018, which is hereby fully incorporated herein by reference.

TECHNICAL FIELD

Embodiments generally relate to circuit protection for electrical systems, and more particularly to an overload protection circuit for monitoring high impedance changes in a non-thermal DC ablation system for prostate treatment.

BACKGROUND

Benign prostatic hyperplasia (BPH) is a common ailment among older men in which the prostate gland becomes enlarged. As the prostate enlarges, it can compress the urethra which in turn can cause extreme discomforts such as excessive urination, uncontrollable urination, incomplete emptying of the bladder, weak urine streams, or painful or bloody urination. Currently, there are various treatment options available for BPH. The level of treatment, however, can vary relative to the extent of discomfort or symptoms experienced. For example, such treatment could include lifestyle changes, drug therapy, non-surgical procedures, or surgical procedures. Surgical treatments of BPH may or may not be minimally invasive. For the surgical methods, access to the prostate may be via the urethra, the perineum, or other route.

Non-minimally invasive surgical treatments include Trans Urethral Resection of the Prostate (TURP). Conducted in an operating room under general or spinal anesthetic, a probe is passed through the urethra which scrapes away prostate tissue causing the blockage. Side effects may include retrograde ejaculation, impotence, and a repeat of the procedure if the blockage regrows.

Minimally invasive surgical treatments usually offer the incentives of less pain, faster recovery, lower costs, and use of local anesthesia and a mild sedative. In general, minimally invasive surgical treatments destroy prostate tissue through one of various mechanisms. The destroyed prostate tissue may be reabsorbed by the body and/or discharged into the urine over a period of time. Minimally-invasive surgical treatment options include generation of heat, freezing, chemical means, ultrasound, and non-thermal ablation to destroy prostate tissue. Examples of non-thermal ablation therapies and systems for treatment of BPH are described in U.S. Pat. Nos. 9,211,155 and 9,597,145, and U.S. Publ. Appl. Nos. 2010/0049192 and 2011/0106072, all of which are commonly owned by the assignee of the present application, and the disclosures of each of which are hereby incorporated by reference.

While providing advantages over conventional surgical treatments for BPH, minimally invasive surgical treatments have other issues that must be addressed. Care must be taken to avoid inadvertent nerve stimulation during minimally invasive treatment. For non-thermal ablation, for example, gas bubbles can form within the prostate tissue, thereby inducing voltage spikes which cause temporary unpleasant sensations to occur within patients. It would be desirable to provide improvements to non-thermal BPH treatment systems that could address these issues.

SUMMARY

Embodiments are directed to systems for controlling impedance swings for a DC ablation non-thermal BPH therapy system that delivers an essentially constant current to electrodes inside the prostate tissue to be removed.

There are two issues that occur with present DC ablation systems involving impedance increases. First, a gas bubble can largely enclose an electrode leading to a sudden short term impedance rise due to the nonconductance of the gas. Second, the tissue near the electrode can become desiccated leading to a gradual increase in impedance. In cases of the first issue, the sudden increase in impedance leads to a rapid voltage increase which can be painful to the patient. In cases of the second issue, the increased impedance reduces the effectiveness of the process by reducing or eliminating the current.

In various embodiments, a protection circuit is provided as part of a DC ablation non-thermal BPH therapy system and includes a power source configured to supply power to the circuit and an overload protection device configured to limit the peak voltage. A capacitor circuit is used to prevent sudden voltage spikes.

In certain embodiments, the protection circuit further includes a switching circuit configured to selectively control a supply path from the power source and the overload protection device. The protection circuit may also include a monitoring circuit comprising a reference unit, wherein the reference unit is configured to provide a reference signal. The protection circuit may further include a controller coupled to the monitoring circuit, wherein the controller is configured to activate the switching circuit based on the reference signal.

In the case of gradual impedance rises from desiccation, the protection circuitry may be configured to modify the pathways for current delivery for the non-thermal BPH therapy.

Some embodiments are directed to a method of restricting excess voltage via a protection circuit. The method generally includes receiving a reference signal characterizing an event of the protection circuit, enabling an overload protection device, and selectively utilizing the overload protection device.

An embodiment is directed to a direct current (DC) prostate ablation therapy system including: a catheter; a power source; an overload protection device; a monitoring circuit; a switching circuit; and a controller. The catheter includes a plurality of electrodes configured to deliver a DC ablation therapy to prostate tissue. The power source is configured to supply a DC current to the plurality of electrodes. The overload protection device is configured to buffer energy from the power source. The monitoring circuit is configured to monitor a voltage of the DC ablation therapy. The switching circuit is configured to selectively control a path of the DC current from the power source to the plurality of electrodes and the overload protection device. The controller is configured to selectively activate the switching circuit in response to the monitoring circuit detecting an undesirable increase in the voltage delivered for the DC ablation therapy.

In certain embodiments, the power source is configured to selectively supply the DC current as a constant current of between 10 to 50 mA of direct current.

In some embodiments, the overload protection device comprises at least one capacitor.

In some embodiments, each of the plurality of electrodes comprises at least one anode and at least one cathode. In some cases, each anode of each of the plurality of electrodes is electrically coupled to the power source via the switching circuit.

An embodiment is directed to a direct current (DC) prostate ablation therapy system including: a catheter; a power source; an overload protection device; a monitoring circuit; a switching circuit; and a controller. The catheter includes a plurality of electrodes configured to deliver a DC ablation therapy to prostate tissue. The power source is configured to supply a DC current to the plurality of electrodes. The overload protection device is configured to buffer energy from the power source. The monitoring circuit is configured to monitor an impedance of the DC ablation therapy. The switching circuit is configured to selectively control a path of the DC current from the power source to the plurality of electrodes and the overload protection device. The controller is configured to selectively activate the switching circuit in response to the monitoring circuit detecting an undesirable change in the impedance for the DC ablation therapy.

An embodiment is directed to a direct current (DC) prostate ablation therapy system including: a catheter; a power source; an overload protection device; a monitoring circuit; a switching circuit; and a controller. The catheter includes a plurality of electrodes configured to deliver a DC ablation therapy to prostate tissue. The power source is configured to supply a DC current to the plurality of electrodes. The overload protection device is configured to buffer energy from the power source. The monitoring circuit is configured to monitor a parameter of the DC ablation therapy. The switching circuit is configured to selectively control a path of the DC current from the power source to the plurality of electrodes and the overload protection device. The controller is configured to selectively activate the switching circuit in response to the monitoring circuit detecting a change in the parameter for the DC ablation therapy indicative of an undesirable increase in an energy being delivered by the DC ablation therapy.

The above summary is not intended to describe each illustrated embodiment or every implementation of the present invention. The detailed description and claims that follow more particularly exemplify these embodiments.

Figure 1:
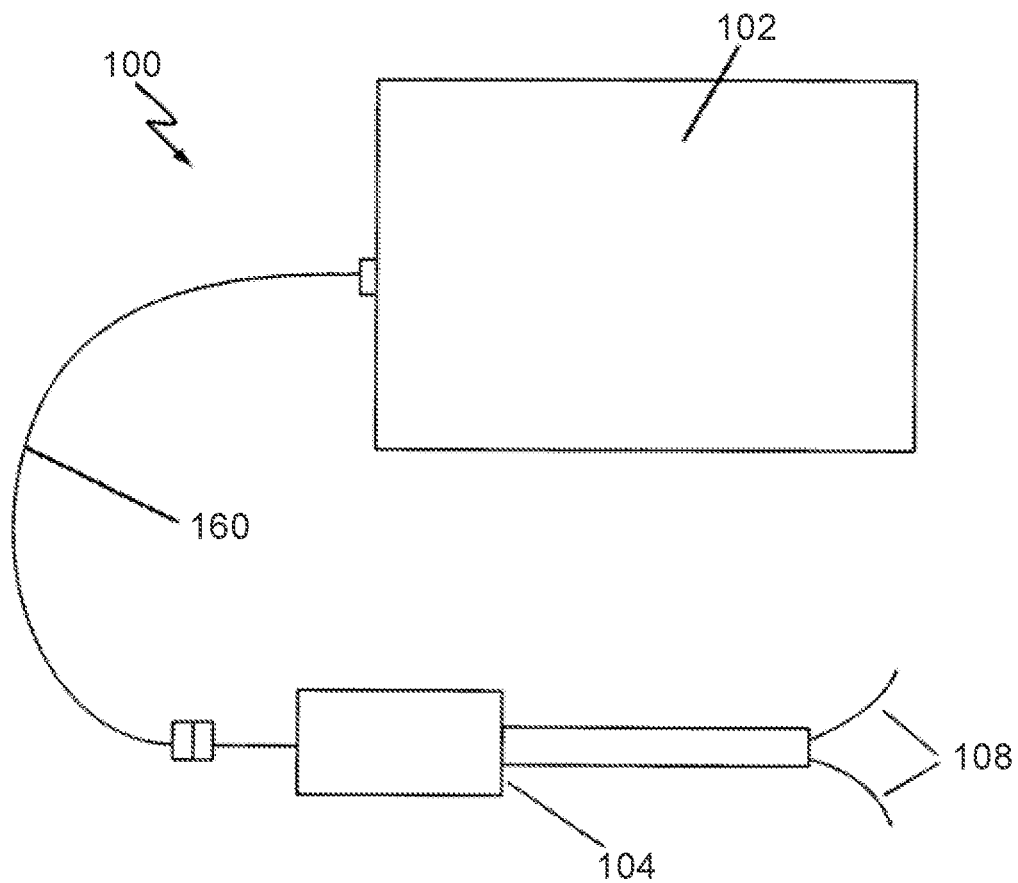
FIG. 1 shows a system for treating tissue, according to an embodiment.

While embodiments are amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DRAWINGS

Referring to FIG. 1, an ablation therapy system comprising a load protection circuit is depicted, according to an embodiment. As shown, system 100 includes a generator 102, electrodes 108, and a catheter 104, which is electrically coupled to generator 102 via cable 160. The catheter 104 may be inserted in the body to a desired location for tissue treatment. Once positioned, the electrodes 108 may be deployed through the catheter 104, while the position of the catheter 104 is maintained utilizing a fixation element. To treat tissue, generator 102 provides power to electrodes 108, which then apply a DC current to a treatment area of the tissue. The tissue is thus treated by DC ablation in a non-thermal manner. As illustrated, the electrodes 108 deploy outwardly from the catheter 104. Such outward deployment may be, for example, radial or may be linear. Generally, the electrodes 108 may be coupled to the catheter 104 or to a support structure in the catheter 104. The electrodes 108 further are configured to resist corrosion. In some embodiments, the electrodes 108 may comprise a Nitinol wire with a corrosion resistant coating. The corrosion resistant coating may be, for example, platinum or platinum-iridium. Additionally, as will be discussed in further detail with reference to FIG. 2, generator 102 comprises a load protection circuit 206, to detect and manage increases in impedance at the electrodes that can be caused by gas bubble formations at the surface of electrodes 108.

Figure 2:
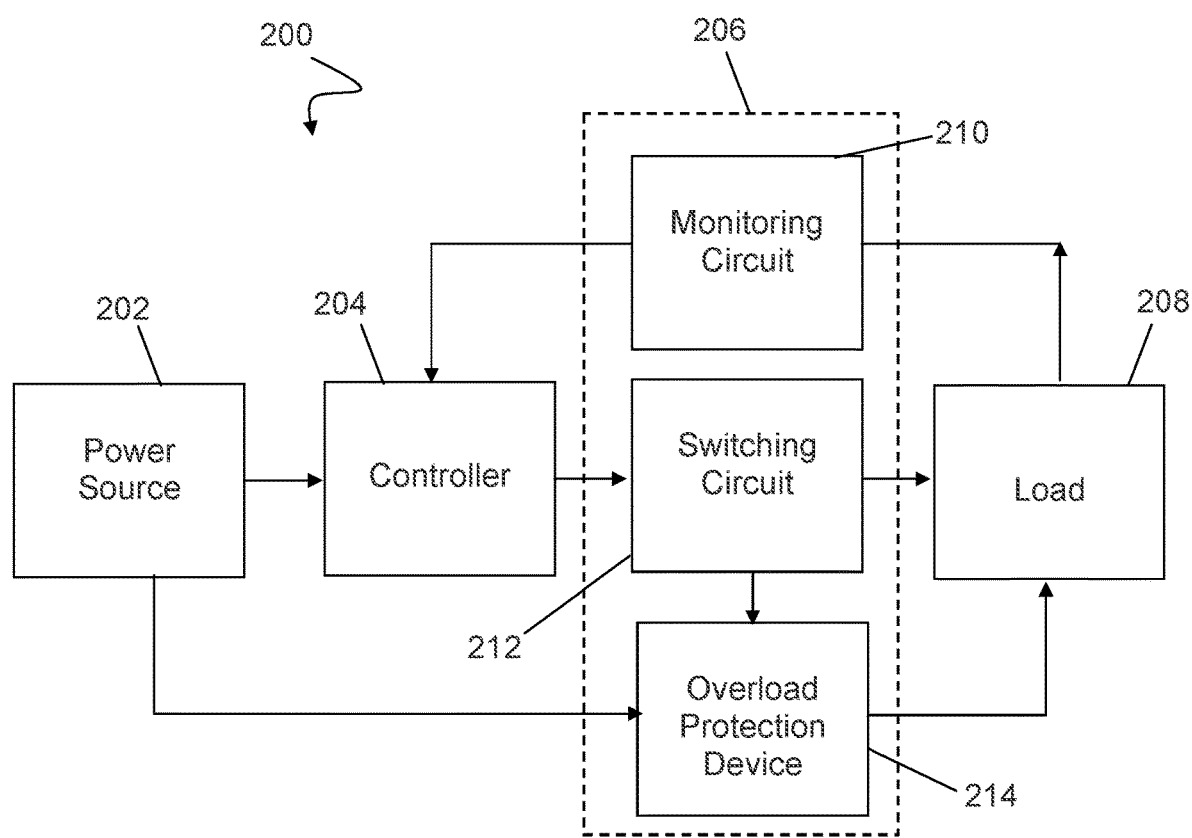
FIG. 2 shows a generator circuit, according to an embodiment with overvoltage protection.

In FIG. 2, a block diagram of a generator circuit 200 is shown according to an embodiment. In embodiments, generator circuit 200 can comprise a power source 202, a controller 204, and a load protection circuit 206 operably coupled to drive an electrode load circuit 208. Power source 202 can comprise a direct current (DC) power source or an alternating current (AC) power source coupled to a converter that converts the AC power to DC power. Controller 204, which is electrically coupled to power source 202 and load protection circuit 206, can comprise analog circuitry, a microprocessor, a field programmable gate array, a programmable logic controller (PLC), and/or other suitable processing components in various embodiments.

In embodiments, load protection circuit 206 can comprise a monitoring circuit 210, a switching circuit 212, and an overload protection device 214 (or other buffer device configured to provide buffer energy to the circuit), which act together to monitor and protect against high impedance load conditions that can arise during treatment. For example, during treatment, as charge is delivered to the electrodes 108, gas formation at the electrode surface or local dehydration, thus leading to increased impedances at the electrode/tissue interface. Monitoring circuit 210 is connected to the electrode load circuit 208 to detect the conditions of load and generate a detection signal VL based on the load condition. In one embodiment, monitoring circuit 210 can be configured to detect the output voltage ($V_{OUT}$) of the electrical load circuit 208, while in other embodiments it can be configured to detect load impedance. In still other embodiments, monitoring circuit 210 can be configured to detect other parameters related to the load current. In embodiments, monitoring circuit 210 can comprise a comparator that compares the output voltage with a predetermined threshold voltage, and generates a control signal to controller 204 based upon the measured condition. For example, when the monitoring circuit 210 detects that the output voltage is above the predetermined threshold (e.g., if gas bubbles have formed at the electrode surface or the treated tissue has become dehydrated), the monitoring circuit 210 sends a control signal to the controller 204 to activate the switching circuit 212. In various embodiments, the comparator can include an operational amplifier, a multiplier, a subtractor, a digital microprocessor, or other suitable detection devices. Additionally, circuit 200 can comprise two or more comparator circuits in other embodiments.

As depicted, monitoring circuit 210 can be coupled to an output of electrode load circuit 208 and an input of switching circuit 212. In embodiments, monitoring circuit 210 can comprise a comparator or other suitable detection device to monitor high impedance conditions at the electrode load circuit 208. In some embodiments, monitoring circuit 210 may further comprise a filtering circuit having resistive-capacitive elements to stabilize the output signal received by load circuit 208.

Figure 3A:
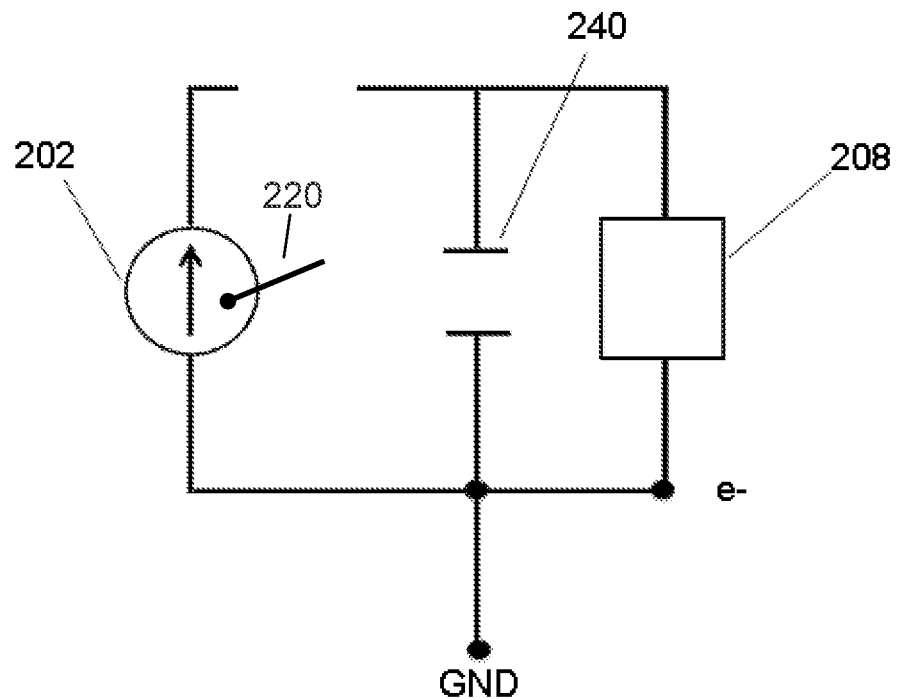
FIG. 3A shows a schematic diagram of an overload protection device, according to a capacitor embodiment.

Switching circuit 212 selectively enables and disables power flow to overload protection device 214 (i.e. buffer) and load circuit 208 based on an output signal of monitoring circuit 210, which generates an overload signal in response to an overload condition. In some embodiments, switching circuit 212 can comprise at least one switch 220 as shown in FIG. 3A. The at least one switch 220 may include, for example, metal-oxide-semiconductor field-effect-transistors (MOSFETs), insulated-gate bipolar transistors (IGBTs), gallium arsenide field-effect transistors (GaAsFETs), Gallium Nitride transistors (GaNFETs), bipolar junction transistors (BJTs), or other suitable active devices. An output of switching circuit 212 is coupled to an input terminal of overload protection device 214 and operates to activate device 214 in response to a detected increase in impedance. In one embodiment, overload protection device 214 can comprise a capacitor 240 coupled in parallel to power source 202 (see FIG. 3A). In particular, switching circuit 212 couples capacitor 240 to power source 202 in a charging position for charging the capacitor, and to an open discharging position for discharging capacitor 240. Those of skill in the art will understand that the specific type and values of capacitor 240 and power source 202 may vary according to design and specification. For example, in various embodiments, capacitor 240 can be sized between approximately 250 µF to 125 mF. In some embodiments, a filter circuit including resistive-capacitive elements may be incorporated into the protection circuit to reduce the electrical noise at the output.

Steady state DC voltage is generally not painful like AC voltage stimulate is as the use of DC voltage tends to not stimulate nerves. However, a sudden increase or decrease in a DC voltage can be painful. Dalziel C F, Massoglia F P, "Let-go currents and voltages," *Transactions of the American Institute of Electrical Engineers, Part II: Applications and Industry.* 1956; 75(2):49-56.

Figure 3B:
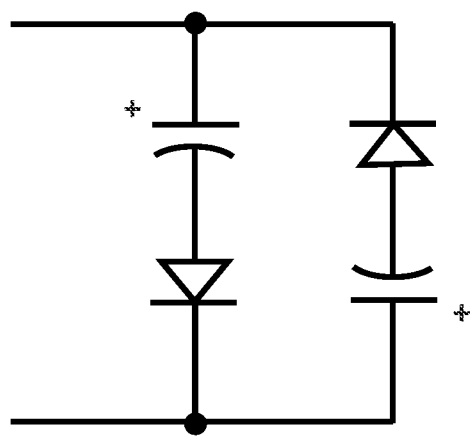
FIG. 3B shows a capacitor embodiment.

FIG. 3B shows the preferred embodiment in which two electrolytic capacitors are connected in series with back biased diodes and anti-parallel configuration. This allows the use of large capacitance values and positive and negative voltages.

$$\Delta V = I \frac{\Delta t}{C}$$

$$C = I \frac{\Delta t}{\Delta V}$$

A typical ablation current is 25 mA and the duration of a gas bubble is 100 ms-10 s. In order to limit the maximum voltage increase to 2 volts the capacitance values will be between:

$$1250 \ \mu F = \frac{25 \ mA \cdot 100 \ ms}{2 \ V}$$

and $$125 \ mF = \frac{25 \ mA \cdot 10 \ s}{2 \ V}$$

Because the primary factor for the pain is dV/dt, even smaller capacitors may be helpful for reducing the pain. To reduce the dV/dt below 100 volts per second, a capacitor of 250 µF will suffice.

Figure 4A:
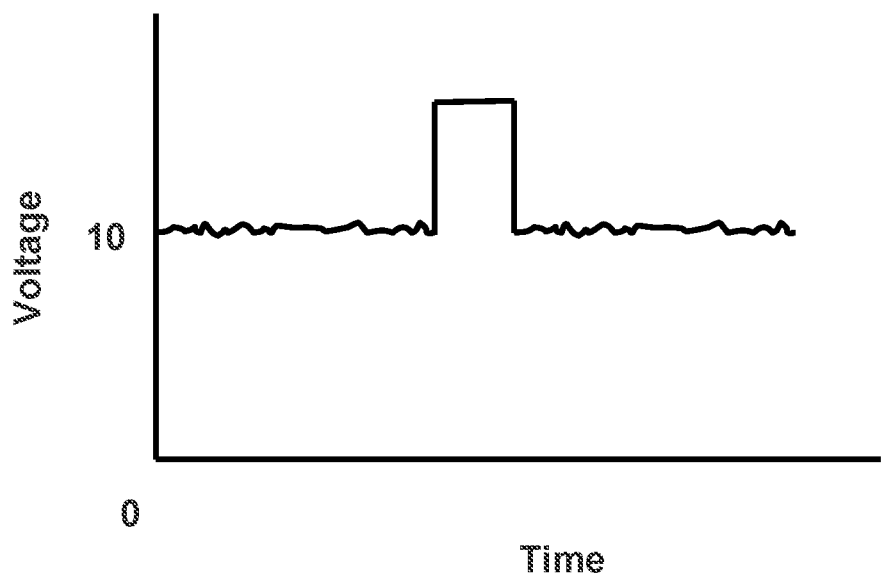
FIG. 4A shows a voltage spike with a gas bubble, according to an embodiment.

FIG. 4A shows a typical voltage being delivered during DC ablation with a sudden increase during gas bubble formation. Since the conventional circuitry delivers a constant current, this voltage will be proportional to the impedance. If the impedance suddenly jumps to a very high value then the output voltage will go to the maximum available from the conventional circuitry.

Figure 4B:
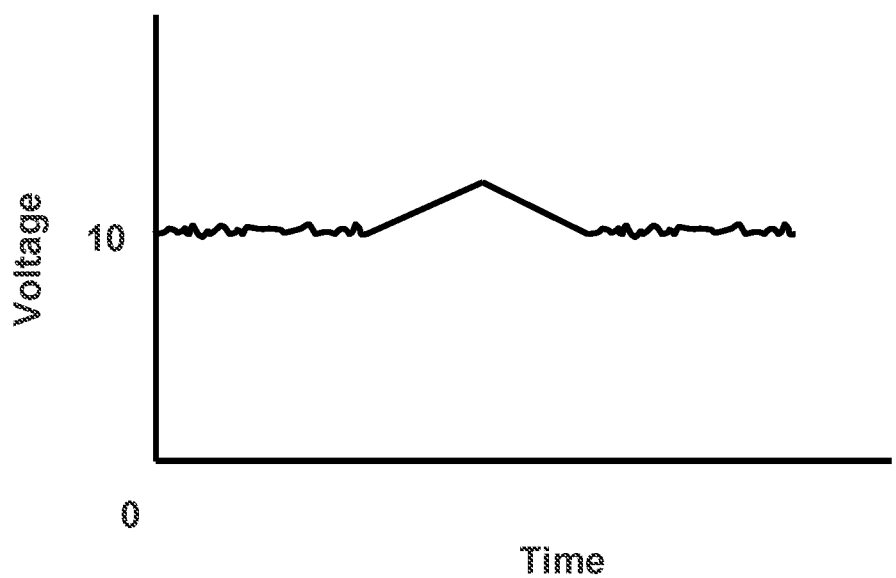
FIG. 4B shows a voltage spike with a gas bubble being reduced with the capacitor embodiment.

FIG. 4B shows the output voltage being delivered during DC ablation with a smaller and slower increase during gas bubble formation with the instant invention.

Figure 5A:
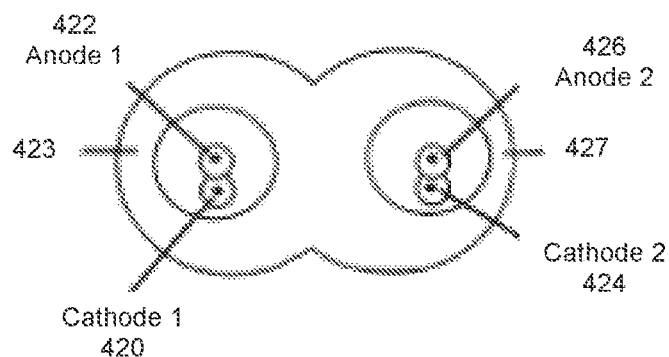
FIG. 5A shows two cathodes in parallel and two anodes in parallel and the associated treatment zones with moderate resistance, according to an embodiment.
Figure 5B:
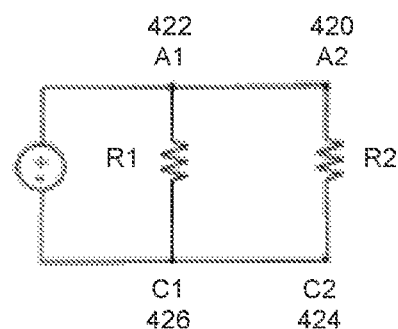
FIG. 5B shows an electrical diagram of FIG. 4A, according to an embodiment.

In other embodiments, referring now to FIGS. 5A and 5B, protection circuit 206 can comprise a series of electrodes electrically coupled in parallel. For example, as shown in FIGS. 5A and 5B, at least one anode pair and at least one cathode pair may be provided in parallel. FIG. 5A illustrates a first anode 422, a second anode 426, a first cathode 420, and a second cathode 424. Although two anodes and two cathodes are illustrated in FIGS. 5A and 5B, it should be noted that, in other embodiments, three or more electrodes may be placed in parallel.

FIG. 5A further illustrates the treatment areas 423 and 427 associated with the anodes and the cathodes. Generally, each electrode of an anode pair or cathode pair may be at approximately the same potential and be placed in close proximity. Providing electrodes in parallel and in close proximity can ensure continued treatment even if one electrode has a high impedance due to local dehydration. More specifically, if one anode (or cathode) of an anode (or cathode) pair loses contact, the area will continue to be treated by the other anode (or cathode) in parallel. Additionally, arranging each electrode pair in parallel allows for each to be independently controlled. In other words, a power source, such as power source 202, may be used to deliver the current for each electrode pair in order to control the charge passing through each electrode and thus the size of the treatment zone. If multiple electrode pairs are placed on a single current source, the treatment zones may be controlled by putting a coulomb counter on each electrode and directing the desired amount of charge to each electrode.

The method of this embodiment will be explained with an example. Imagine that anode 1 422 has local desiccation and its impedance slowly rises. The circuitry will note that the voltage is increasing in pathway 1 (anode 1 to cathode 1) and thus diagnose a desiccation in that pathway. Circuitry must now determine which of the two electrodes is the culprit. A test "cross-current" is now passed from anode 1 to cathode 2. If this is passed with atypical voltage then it is verified that anode 1 is not the culprit and that cathode 1 is the problem. The output circuit is then reconfigured so that anode 1 is ignored and only anode 2 is used for current delivery while cathodes 1 and 2 are used in parallel for the return. In a similar manner, anode 1 will be tested for impedance every 1-10 seconds so it can be reused as soon as there is a re-infiltration of bodily fluids.

Note that during the temporary current delivery scheme of this embodiment, about ¾ of the tissue is still receiving DC ablation since three of the four electrodes are active.

Referring now back to FIG. 2, in operation, monitoring circuit 210 monitors the rate of change of voltage (dV/dt) of electrode load circuit 208 and prevents the voltage from rising in the event of a voltage spike in one embodiment. In other words, if dV/dt of the electrode load circuit is greater than a threshold level, a high impedance condition (i.e., bubble formation) is indicated and switching circuit 212 enables a discharge of the overload protection device 214, thereby limiting the voltage rise (dV/dt) at the output in relation to the discharge rate of the overload protection capacitor.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112(f) of 35 U.S.C. are not to be invoked unless the specific terms "means for" or "step for" are recited in a claim.

The invention claimed is:

1. A direct current (DC) prostate ablation therapy system comprising:
    a catheter including a plurality of electrodes configured to deliver a DC ablation therapy to prostate tissue;
    a power source configured to supply a DC current to the plurality of electrodes;
    an overload protection device configured to buffer energy from the power source;
    a monitoring circuit configured to monitor a voltage of the DC ablation therapy;
    a switching circuit configured to selectively control a path of the DC current from the power source to the plurality of electrodes and the overload protection device; and
    a controller configured to selectively activate the switching circuit in response to the monitoring circuit detecting an undesirable increase in the voltage delivered for the DC ablation therapy.

2. The system of claim 1, wherein the power source is configured to selectively supply the DC current as a constant current of between 10 to 50 mA of direct current.

3. The system of claim 1, wherein the overload protection device comprises at least one capacitor.

4. The system of claim 1, wherein each of the plurality of electrodes comprises at least one anode and at least one cathode.

5. The system of claim 4, wherein each anode of each of the plurality of electrodes is electrically coupled to the power source via the switching circuit.

6. A direct current (DC) prostate ablation therapy system comprising:
    a catheter including a plurality of electrodes configured to deliver a DC ablation therapy to prostate tissue;
    a power source configured to supply a DC current to the plurality of electrodes;
    an overload protection device configured to buffer energy from the power source;
    a monitoring circuit configured to monitor an impedance of the DC ablation therapy;
    a switching circuit configured to selectively control a path of the DC current from the power source to the plurality of electrodes and the overload protection device; and
    a controller configured to selectively activate the switching circuit in response to the monitoring circuit detecting an undesirable change in the impedance for the DC ablation therapy.

7. A direct current (DC) prostate ablation therapy system comprising:
    a catheter including a plurality of electrodes configured to deliver a DC ablation therapy to prostate tissue;
    a power source configured to supply a DC current to the plurality of electrodes;
    an overload protection device configured to buffer energy from the power source;
    a monitoring circuit configured to monitor a parameter of the DC ablation therapy;
    a switching circuit configured to selectively control a path of the DC current from the power source to the plurality of electrodes and the overload protection device; and a controller configured to selectively activate the switching circuit in response to the monitoring circuit detecting a change in the parameter for the DC ablation therapy indicative of an undesirable increase in an energy being delivered by the DC ablation therapy.

* * * * *